United States Patent

Scheu

[11] Patent Number: 5,879,157
[45] Date of Patent: Mar. 9, 1999

[54] HERBST MECHANISM

[75] Inventor: Christian Scheu, Iserlohn, Germany

[73] Assignee: Scheu Dental, Iserlohn, Germany

[21] Appl. No.: 967,714

[22] Filed: Nov. 10, 1997

[30] Foreign Application Priority Data

Nov. 9, 1996 [DE] Germany .................. 296 19 489 U

[51] Int. Cl.⁶ .................................................. A61C 3/00
[52] U.S. Cl. ................................................................ 433/19
[58] Field of Search .............................. 433/18, 19, 21

[56] References Cited

U.S. PATENT DOCUMENTS

| | | | |
|---|---|---|---|
| 1,202,798 | 10/1916 | Canning | 433/21 |
| 3,798,773 | 3/1974 | Northcutt | 433/19 |
| 4,795,342 | 1/1989 | Jones | 433/19 |
| 4,969,822 | 11/1990 | Summer | 433/19 |
| 5,352,116 | 10/1994 | West | 433/19 |
| 5,378,147 | 1/1995 | Mihailowitsch | 433/19 |
| 5,401,168 | 3/1995 | Magill | 433/18 |
| 5,562,445 | 10/1996 | DeVincenzo et al. | 433/19 |
| 5,678,990 | 10/1997 | Rosenberg | 433/19 |
| 5,711,667 | 1/1998 | Vogt | 433/19 |
| 5,738,514 | 4/1998 | DeVincenzo et al. | |

*Primary Examiner*—Ralph A. Lewis
*Attorney, Agent, or Firm*—Anderson, Kill & Olick, P.C.

[57] ABSTRACT

A mechanism for applying a positioning force between upper and lower jawbone, and including an outer telescopic element and an inner telescopic element displaceable within the outer telescopic element, with the outer and inner telescopic elements having each an eyelet for connection to a teeth brace, and with an arrangement which prevents the inner telescopic element from being pull-out of the outer telescopic element.

12 Claims, 2 Drawing Sheets

HERBST MECHANISM

BACKGROUND OF THE INVENTION

1. Field of the Invention

The present invention relates to a mechanism for applying a positioning force between upper and lower jawbone, with the mechanism including an outer telescopic element and an inner telescopic element displaceable within the outer telescopic element, and with the outer and inner telescopic elements having each an eyelet for connection to a teeth brace.

2. Description of the Prior Art

Mechanisms of the above-described type, such as, e.g., disclosed in U.S. Pat. No. 4,551,095 or in European publication EP-O 128 744-B1, serve for moving the low jawbone relative to the outer jawbone anteriorly or posteriorly. Such mechanisms are being used more and more in orthodontic applications. These mechanisms include double plates, Herbst hinges or other bimaxillar mechanisms. The essential requirement these mechanisms should meet consists in that they should provide for an individual stepwise positioning of the low jawbone relative to the upper jawbone by using two telescopic elements displaceable relative to each other.

In the known mechanisms, an inner telescopic element is displaced in a hollow outer element, with both elements being attached to teeth braces of the lower and upper jawbones. The drawback of these mechanisms consists in that the two elements can separate from each other. Such separation leads to that the mechanisms cannot function properly and can result in injury of the inner cheek of a patient.

Accordingly, an object of the present invention is to provide a mechanism of the above-described type in which a danger of separation of the two telescopic elements is eliminated.

Another object of the present invention is to provide a mechanism of the above-described type which would insure an adaptation of the mechanism to the individual low jawbone position of a patient before installation of the mechanism in place.

SUMMARY OF THE INVENTION

These and other objects of the present invention, which will become apparent hereinafter, are achieved by providing means which prevents the separation of the two telescopic elements from each other.

Further, according to the present invention, there is provided means which permits to longitudinally adjust a position of one of the connection eyelets relative to the other of the connection eyelets. The adjusting means generally comprises a threaded member connected with the adjustable eyelet and cooperating with thread means, which remain stationary during the adjustment process.

The prevention of the separation of the two telescopic elements from each other eliminates a danger of injury to the patient. Furthermore, the possibility of adjustment of the relative position of the connection eyelets permits to conduct the treatment of the patient in several phases, without the need in the alteration of the entire mechanism in a laboratory. A dentist can perform the necessary adjustment directly on the patient.

According to a further development of the present invention, the outer telescopic element is formed as a sleeve with an elongate guide slot, and the inner telescopic element is formed as a telescopic rod having, at its end extending into the sleeve, a member extending into the slot. Alternatively, the end of the telescopic end itself can be bent out and extended into the slot. The latter construction is particularly simple and effective, as it does not require any additional fabrication steps. At that, the bent-out end of the telescopic rod simultaneously serves as a guiding element. Other solutions are also possible In order to enable the bending of the telescopic rod end and its insertion, the slot is open at its end adjacent to the eyelet associated with the outer telescopic element.

According to another embodiment of the present invention, the outer telescopic element is formed as a hollow cylinder within which an inner telescopic nut, in which an eyelet carrying threaded rod is received, is longitudinally displaceable, with another stationary nut being secured therein. At that, the stationary nut receives a further threaded rod carrying the other of the connection eyelets.

BRIEF DESCRIPTION OF THE DRAWINGS

The features and objects of the present invention with become more apparent, and the invention itself will be best understood from the following detailed description of the preferred embodiments when read with reference to the accompanying drawings, wherein.

DETAILED DESCRIPTION OF THE PREFERRED EMBODIMENTS

Figure 1:
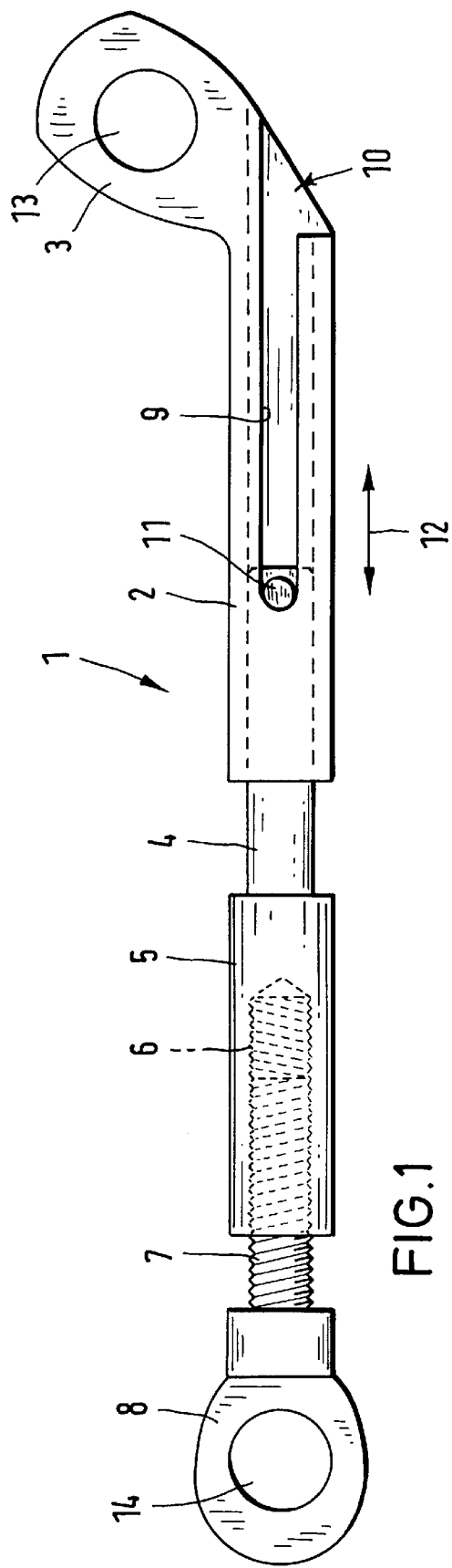
FIG. 1 shows a side view of a first embodiment of a Herbst mechanism accordingly to present invention.

A Herbst mechanism according to the present invention, which is shown in FIG. 1, is generally designated with a reference numeral 1 and includes a sleeve 2 with an angularly offset connection eyelet 3 and a telescopic rod 4. The telescopic rod 4 is provided with a thread bushing 5 having an inner thread 6 for receiving a threaded rod 7 connected with a second connection eyelet 8 at a free end thereof.

The sleeve 2 has an elongate slot 9 which is open at side thereof adjacent to the first eyelet 3.

The telescopic rod 4 is provided with a guiding pin 11 which slides in the guide slot 9 so that the rod 4 is displaceable in the sleeve 2 in directions indicated by a double arrow 12. In an expanded position, e.g., in the maximum expanded position which is shown in FIG. 1, the operating distance of the centers of two locating holds 13 and 14 in the eyelets 3 and 8 respectively, can be so changed or adjusted that the eyelet 8 would rotate, causing the displacement of the threaded rod 7 in the thread bushing 5. In a use position, the guiding pin 11 serves as a pull-out prevention member, which prevents the telescopic rod 4 from being pulled out of the sleeve 2.

Figure 2:
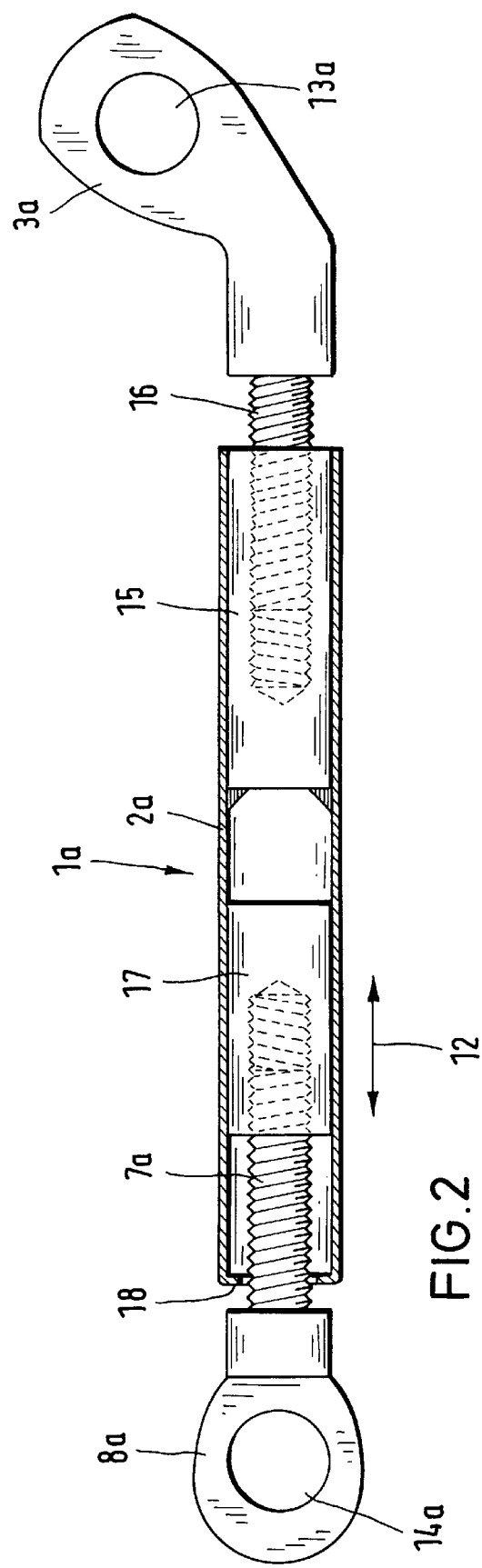
FIG. 2 shows a side, partially cross-sectional, view of a second embodiment of a Herbst mechanism according to the present invention.

FIG. 2 shows a modified embodiment of the Herbst mechanism according to the invention, where similar elements are designated with the same references as in FIG. 1 with an index "a". In the embodiment shown in FIG. 2, the outer telescopic element 2a is formed as a substantially hollow cylinder having at one side thereof a nut 15 fixedly secured therein. The nut 15, e.g., can be welded to the cylinder. The nut 15 serves for receiving the threaded rod 16 with an eyelet 3a.

Inside of the outer telescopic element 2a, there is provided another telescopic nut 17 which is engaged by a threaded rod 7a provided with an eyelet 8a. The end stop 18 serves to prevent the pull-out of the nut 17. The operating distance between the locating holes 13a and 14a of the eyelets 3a and 8a is adjustable in the same manner as in the embodiment show in FIG. 1.

Figure 3:
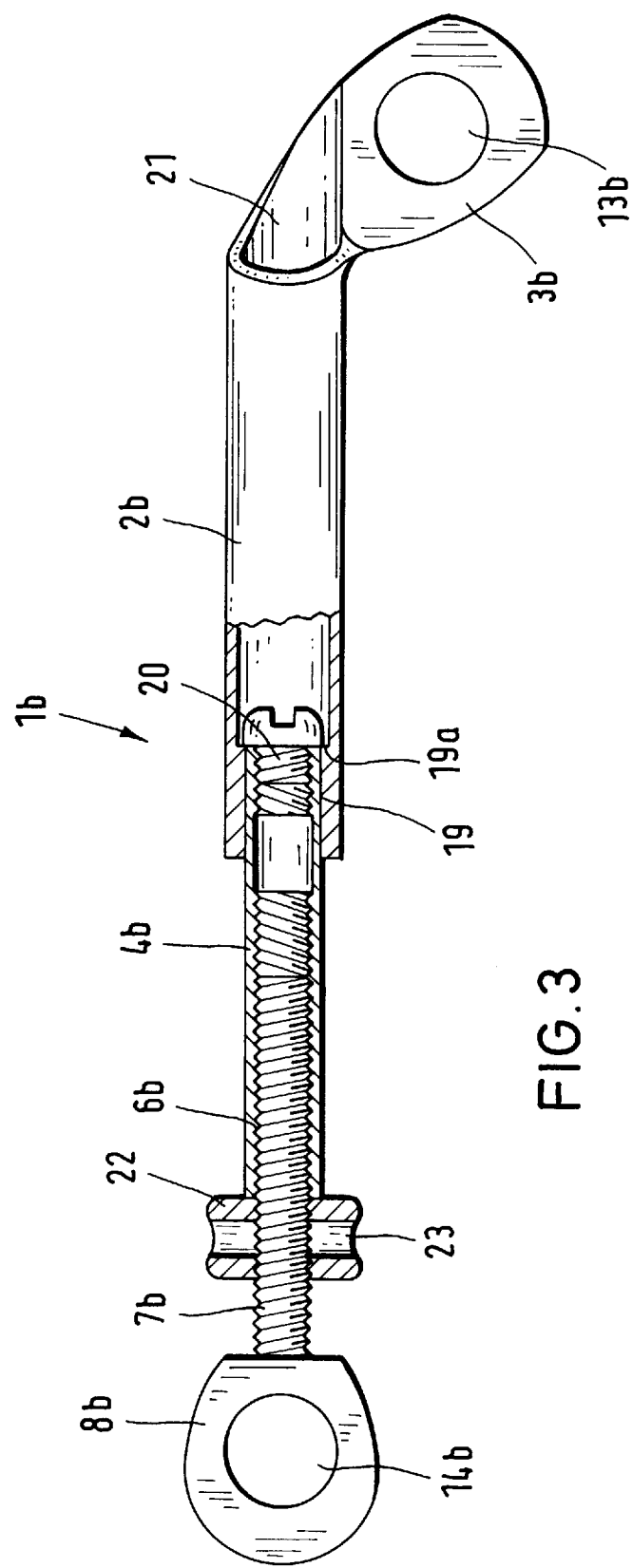
FIG. 3 shows a side, partially cross-sectional view, of a third embodiment of a Herbst mechanism according to the present invention.

A still further embodiment of a Herbst mechanism is shown in FIG. 3 where the elements similar to those of FIGS. 1 and 2 are designated with the same reference numerals with an index "b". The Herbst mechanism 16 includes an outer sleeve 26 with an angularly offset connection eyelet 3b, and a telescopic rod 4b displaceable in the sleeve 2b. The telescopic rod 4b has an inner thread 6b for receiving a threaded rod 7b which carries another connection eyelet 8b.

The sleeve 2b has a cylindrical region 18 corresponding to an outer diameter of the telescopic rod 4b. At that, the diameter of the cylindrical region 18 is smaller than the inner diameter of the remaining portion of the sleeve 2b. Thereby, a stop shoulder is formed. The telescopic rod 4b is provided, at its end received in the sleeve 2b, with a screwed-in stop screw 20 which is inserted through the access opening 21 in the sleeve 2b.

The sleeve 2b instead of its own thread, can be provided with an attachment member 22 having a circular bore 23 for providing access to the threaded rod 7b in the telescopic rod 4b. This embodiment permits to adjust an operating distance between the locating holes 13b and 14b of the connection eyelets 3b and 8b even when the Herbst mechanism is placed into the mouth of a patient. It is to be noted that the stop screw 20 insure quick disassembly of the Herbst mechanism. For separating the telescopic rod 4b from the sleeve 2b, it is sufficient to simply unscrew the stop screw 20 from the telescopic rod 4b.

The present invention is not limited to a particular shape of the connection eyelets or their arrangement relative to each other. No the inventive Herbst mechanism is limited to the use of particular material. However, it is to be noted that because of the use of the inventive mechanism in the field of dentistry, the use of a nickel-free steel is recommended.

Thus, though the present invention was shown and described with reference to the preferred embodiments, various modifications thereof will be apparent to those skilled in the art and, therefore, it is not intended that the invention be limited to the disclosed embodiment or details thereof, and departure can be made therefrom within the spirit and scope of the appended claims.

What is claimed is:

1. A mechanism for applying a positioning force between upper and lower jawbones, the mechanism comprising:
    an outer telescopic element and an inner telescopic element displacement within the outer telescopic element, the outer and inner telescopic elements having each an eyelet for connection to a teeth brace; and
    means for preventing the inner telescopic element from being pulled-out of the outer telescopic element,
    wherein the inner telescopic element is formed as a sleeve provided with an inner thread for receiving a threaded rod carrying the associated connection eyelet, the sleeve being further provided, at an end thereof remote from the outer telescopic element, with an attachment member for enabling access to the threaded rod.

2. A mechanism as set forth in claim 1, wherein the attachment member has an inner thread cooperating with an outer thread of the threaded rod.

3. A mechanism as set forth in claim 1, wherein the attachment member has a circular opening for enabling access to the threaded rod.

4. A mechanism as set forth in claim 1, wherein the outer telescopic elements is formed as a sleeve, and wherein the pull-out preventing means comprises an inner shoulder provided in the sleeve forming the outer telescopic element, and the sleeve forming the inner telescopic element has, at an end thereof remote from the connection eyelet associated with the inner telescopic element, a stop screw cooperating with the shoulder.

5. A mechanism as set forth in claim 4, wherein the sleeve forming the outer telescopic element has an access opening for enabling access to the stop screw.

6. A mechanism for applying a positioning force between upper and lower jawbones, the mechanism comprising;
    an outer telescopic element and an inner telescopic element displaceable within the outer telescopic element, the outer and inner telescopic elements having each an eyelet for connection to a teeth brace; and
    means for preventing the inner telescopic element from being pulled-out of the outer telescopic element,
    wherein the inner telescopic element is formed of a sleeve with a smooth inner surface and having, at an end thereof remote from the outer telescopic member, an attachment member having an inner thread, and of a threaded rod extending through the attachment member into the sleeve and carrying at an end thereof remote from the sleeve the connection eyelet associated with the inner telescopic member.

7. A mechanism as set forth in claim 6, wherein the attachment member has a circular opening for enabling access to the threaded rod.

8. A mechanism as set forth in claim 6, wherein the outer telescopic element is formed as a sleeve, and wherein the pull-out preventing means comprises an inner shoulder provided in the sleeve forming the outer telescopic element, and the sleeve forming the inner telescopic element has, at an end thereof remote from the connection eyelet associated with the inner telescopic element, a stop screw cooperating with the shoulder.

9. A mechanism as set forth in claim 8, wherein the sleeve forming the outer telescopic element has an access opening for enabling access to the stop screw.

10. A mechanism for applying a positioning force between upper and lower jawbones, the mechanism comprising:
    an outer telescopic element and an inner telescopic element displaceable within the outer telescopic element, the outer and inner telescopic elements having each an eyelet for connection to a teeth brace; and
    means for preventing the inner telescopic element from being pulled-out of the outer telescopic element,
    wherein the pull-out prevent means comprises a guide slot formed in the outer telescopic element, and a pull-out preventing member provided at an end of the inner telescopic element which extends into the outer telescopic element, and extending into the guide slot, and
    wherein the guide slot is open at an end thereof adjacent to the connection eyelet carried by the outer telescopic element.

11. A mechanism for applying a positioning force between and lower jawbones, the mechanism comprising:
    an outer telescopic element and an inner telescopic element displaceable within the outer telescopic element, the outer and inner telescopic elements having each an eyelet for connection to a teeth brace; and means for preventing the inner telescopic element from being pulled out of the outer telescopic element, wherein the inner telescopic element is formed as a telescopic rod and has at an end thereof projecting from the outer telescopic element a bushing with an inner thread for receiving a threaded rod carrying at end thereof remote from the bushing the connection eyelet.

12. A mechanism for applying a positioning force between upper and lower jawbones, the mechanism comprising:

an outer telescopic element and an inner telescopic element displaceable within the outer telescopic element, the outer and inner telescopic elements having each an eyelet for connection to a teeth brace; and means for preventing the inner telescopic element from being pulled-out of the outer telescopic element, wherein the outer telescopic element is formed as a hollow cylinder, and the inner telescopic element is formed of a nut, which is displaceable in the hollow cylinder, and a threaded rod engaging the nut and carrying, at an end thereof remote from the nut, the connection eyelet, and wherein the outer telescopic element comprises a further nut secured in the hollow cylinder and a further threaded rod engaging the further nut and carrying, at an end thereof remote from the further nut, the connection eyelet.

* * * * *